United States Patent [19]
Strickland et al.

[11] Patent Number: 5,786,187
[45] Date of Patent: Jul. 28, 1998

[54] METHOD FOR REDUCING NEURONAL DEGENERATION ASSOCIATED WITH SEIZURE

[75] Inventors: Sidney Strickland; Styliani-Anna Tsirka; David G. Amaral, all of Setauket, N.Y.

[73] Assignee: The Research Foundation of State University of New York, Albany, N.Y.

[21] Appl. No.: 531,595

[22] Filed: Sep. 21, 1995

[51] Int. Cl.[6] .......................... C12N 15/00; A61K 38/49
[52] U.S. Cl. ...................... 435/172.1; 435/212; 435/219; 424/94.64; 424/130.1; 514/2
[58] Field of Search .................... 424/94.63, 94.64, 424/130.1; 514/2; 435/212, 219, 172.1

[56] References Cited

PUBLICATIONS

Strickland S, Huarte J, Belin D, Vassalli A, Rickles RJ, Vassalli JD; "Antisense RNA directed against the 3' noncoding region prevents dormant mRNA activation in mouse oocytes", *Science* 241:680–84 (1988).

Qian Z, Gilbert ME, Colicos MA, Kandel ER, Kuhl D; "Tissue–plasminogen activator is induced as an immediate–early gene during seizure, kindling and long–term potentiation", *Nature* 361:453–57 (1993).

Carroll PM, Tsirka SE, Richards WG, Frohman MA, Strickland S; "The mouse tissue plasminogen activator gene 5' flanking region directs appropriate expression in development and a seizure–enhanced response in the CNS" *Development* 120:3173–83 (1994).

Streit WJ; "Microglial–Neuronal Interactions", *Journal of Chemical Neuroanatomy*, 6:261–66 (1993).

Krystosek A, Seeds NW; "PLasminogen Activator Release at the Neuronal Growth Cone", *Science*, 213: 1532–34 (1981).

Sallés FJ, Schechter N, Strickland S.; "A plasminogen activator is induced during goldfish optic nerve regeneration", *The EMBO Journal*, 9(8):2471–77 (1990).

Krystosek A, Seeds NW; "Plasminogen activator secretion by granule neurons in cultures of developing cerebellum", *Proc. Natl. Acad. Sci. USA* 78(12):7810–14 (1981).

Sappino AP, Madani R, Huarte J, Belin D, Kiss JZ, Wohlwend A, Vassalli JD; "Extracellular Proteolysis in the Adult Murine Brain", *J. Clin. Invest.*, 92: 679–85 (1993).

Andersson PB, Perry VH, Gordon S; "Kinetics and Morphological Characteristics of the Macrophage–Microglial Response to Kainic Acid–Induced Neuronal Degeneration", *Neuroscience*, 42(1):201–14 (1991).

Thanos S; "The Relationship of Microglial Cells to Dying Neurons During Natural Neuronal Cell Death and Axotomy–induced Degeneration of the Rat Retina", *European Journal of Neuroscience*, 3: 1189–07 (1991).

Carmeliet P, Schoonjans L, Kieckens L, Ream B, Degen J, Bronson R, DeVos R, van den Oord JJ, Collen D, Mulligan RC; "Physiological consequences of loss of plasminogen activator gene function in mice", *Nature*, 368: 419–24 (1994).

Lawson LJ, Perry VH, Gordon S; "Turnover of Resident Microglia in the Normal Adult Mouse Brain", *Neuroscience*, 48(2):405–15 (1992).

Pollard H, Marlangue CC, Cantagrel S, Represa A, Robain O, Moreau J, Ben–Arie Y; "Kainate–Induced Apoptotic Cell Death in Hippocampal Neurons" *Neuroscience*, 63(1):7–18, (1994).

Meda L, Cassatella MA, Szendrei GL, Otvos Jr. L, Baron P, Villalba M, Ferrari D, Rossi F; "Activation of microglial cells by β–amyloid protein and interferon–γ", *Nature*, 374:647–50 (1995).

Kingston IB, Castro MJM, Anderson S; "In vitro stimulation of tissue–type plasminogen activator by Alzheimer amyloid β–peptide analogues", *Nature Medicine*, 1(2): 138–42 (1995).

Smeyne RJ, Schilling K, Robertson L, Luk D, Oberdick J, Curran T, Morgan JI; "Fos–IacZ Transgenic Mice: Mapping Sites of Gene Induction in the Central Nervous System", *Neuron*, 8: 13–23 (1992).

Golarai G, Cavazos JE, Sutula TP; "Activation of the dentate gyrus by pentylenetetrazol evoked seizures induces mossy fiber synaptic reorganization", *Brain Research*, 593: 257–264 (1992).

Tsirka, S. E., et al. (1995) Nature 337, 340–344.

Roberts–Lewis, J. M., et. al. (1994) J. Neurosci. 14(6), 3934–3944.

Tominaga, K., et. al. (1995) Adv. Exp. Med. Biol. 362, 341–343.

Rami, A., et. al. (1993) Chem. Abst. 119: 62691k.

Murtomaki, S., et. al. (1995) Dev. Biol. 168, 635–648.

*Primary Examiner*—Charles L. Patterson, Jr.
*Attorney, Agent, or Firm*—Hoffmann & Baron, LLP

[57] ABSTRACT

The invention provides a method for regulating neuronal degeneration resulting from injury to nervous tissue. The method includes regulating the expression or activity of protease, preferably tissue-type plasminogen activator (tPA), by microglial cells. Alternatively, the method involves regulating microglial activation in response to injurious conditions. The method, in an alternative embodiment, includes detecting tPA expression or activity, or detecting microglial activation. In addition, the method includes assessing the susceptibility of a human or animal subject to seizure, and may involve detecting the activity or expression of tPA, and may further involve comparing a measured level of tPA expression or activity with a reference level associated with a given probability of seizure.

16 Claims, 13 Drawing Sheets

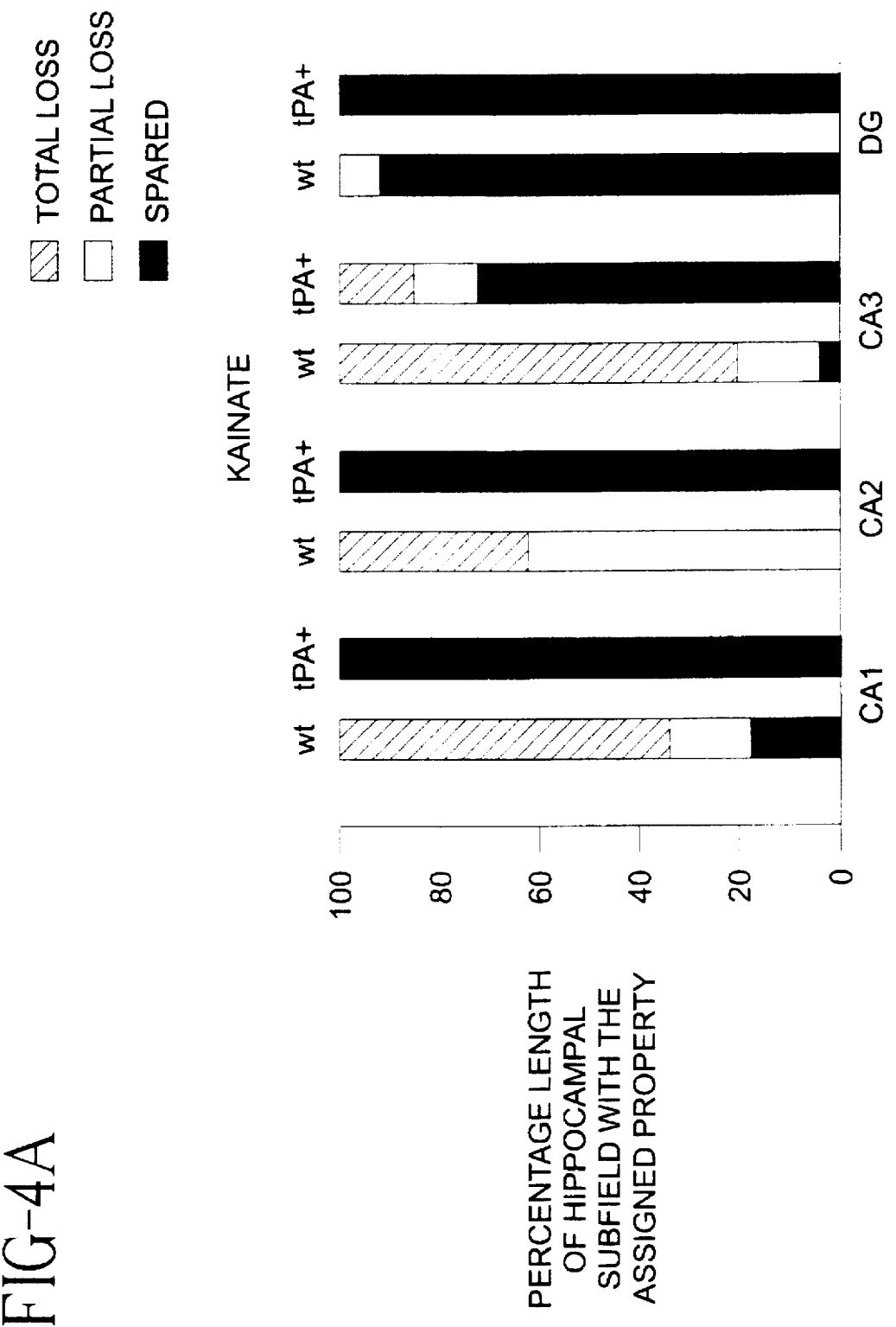

METHOD FOR REDUCING NEURONAL DEGENERATION ASSOCIATED WITH SEIZURE

This invention was made with Government support under Grant No. HD17875 awarded by the National Institutes of Health. The Government has certain rights in this invention.

BACKGROUND OF THE INVENTION

Morphological changes occur in the adult vertebrate brain both during normal learning and in various neuropathologies such as epilepsy and Alzheimer's disease (Refs. 1–3). These changes include neurodegeneration and more subtle remodeling of the cellular architecture, and require modulation of cellular contacts and the extracellular environment. It has been proposed that proteolytic enzymes may be an important mediator in these alterations (Refs. 4, 5). The mechanisms involved in such changes have not previously been identified.

Tissue-type plasminogen activator (tPA), a serine protease which converts inactive plasminogen to the active protease plasmin, is expressed in the adult murine brain (Refs. 6–8). tPA is an immediate-early response gene after induction of neuronal activity: it is transcriptionally induced in the rat and mouse hippocampus either after chemical induction of seizure or after electrical stimulation applied using kindling or long-term potentiation protocols (Refs. 8, 9). In fact, in neural tissues the activity of tPA has been correlated with neurite outgrowth (Ref. 10), regeneration (Ref. 11), and migration (Ref. 12). Nonetheless, tPA has not previously been found to possess any function with respect to neuronal degeneration or pathology.

Microglia are non-neuronal macrophage-like cells present in the developing and adult central nervous systems. Upon neuronal injury, microglia are transformed from a resting state to an activated state, characterized by changes in morpohology, immunophenotype, migration, and proliferation (Refs. 13, 14). Activated microglia participate in the phagocytosis of neurons, and, furthermore, microglial proteases are involved in neuronal degradation (Ref. 15). However, none of these studies has found that tPA in any way mediates the neuronal degradation associated with microglial activity. The mechanisms of such degeneration have remained unelucidated.

As a result, there exists a need for means for inhibiting neuronal degeneration attendant upon seizures and other injurious phenomena in the nervous system. In addition, there exists a need for assessing the potential or actual degeneration of neurons in situations in which such damage is believed to occur. The present invention effectively addresses these and other needs for the first time.

SUMMARY OF THE INVENTION

In one embodiment of the invention, there is provided a method for regulating, preferably inhibiting, neuronal degeneration in a human or animal subject. The method includes regulating, again preferably inhibiting, the function of protease in nervous tissue of the subject. In the preferred case, the protease whose function is regulated is tPA.

The regulation of protease activity can include regulation of protease expression or activity. For example, the regulating may include inhibiting the activity of the tPA enzyme by administering to the subject an effective amount of an inhibitor of tPA activity. The inhibitor may act in any known manner to inhibit tPA activity, including competitive inhibition, etc., and may inhibit tPA activity temporarily or irreversibly. Preferably, the inhibitor is capable of traversing the blood-brain barrier or is otherwise capable of entry into the nervous tissue desired to be treated, e.g., the central nervous system. In this case, the inhibitor may be administered to the subject at a convenient body site remote from the nervous tissue. Alternatively, the inhibitor may be administered directly into nervous tissue, although such procedures may be undesirably complex.

Alternatively, the regulation of protease, e.g., tPA, may be accomplished by inhibiting the expression of tPA. This can be achieved by means of numerous techniques which are known in the art concerning the expression of other genes. For example, regulation in this embodiment can be accomplished by regulating the transcription of a gene encoding tPA, or by regulating the translation of mRNA encoding tPA. Alternatively, this method can involve regulating post-translational processing or transport of the tPA gene product.

Applicants have observed that microglial activation is an event which is intimately associated with neuronal degeneration mediated by tPA. Thus, the method of the invention may include regulation of protease function by regulating microglial activation. For example, an inhibitor of microglial activation may be administered to the subject at a time suitable for preventing or suppressing microglial activation. Such inhibitors are known in the art, and include compounds such as NMDA receptor antagonists, including the non-competitive antagonist MK-801.

The methods of the invention are suitable for regulation of neuronal degeneration in nervous tissue wherever such degeneration is mediated by tPA. Such degeneration is typically observed following insult or injury in central nervous system tissue, more commonly brain tissue. The method is particularly well adapted for use in inhibiting neuronal degeneration in hippocampal tissue.

The invention further includes a method of detecting neuronal degeneration in nervous tissue. This method includes measuring the expression or activity of tPA in nervous tissue. In a preferred case, the method involves detecting such expression or activity in nervous tissue of a human or animal subject, but the method is capable of performance in vitro, such as with regard to neuronal tissue culture. Alternatively, for tissue samples or pathological specimens, the method may be performed relative to a tissue specimen by application of a staining-type technique.

In this method, a level of expression or activity of tPA is measured in an in vivo or in vitro system being investigated. This measured amount is compared with a reference amount of tPA expression or activity. Such reference measurement can be, for example, an accepted normal level or a previous test level. The difference measured is then correlated with known specific amount of neuronal degeneration. A determination can then be made which establishes whether and to what degree the expression of activity of tPA is to be regulated.

In this method, tPA expression and/or activity may be detected and measured either directly or indirectly. One exemplary indirect method involves detecting the level of microglial activation in the nervous tissue of interest. This may be accomplished by measuring expression of a cell surface marker expressed only by activated microglia by means of antisera, which may be directly or indirectly detected through detectable label moieties. Other methods may be employed which take advantage of metabolic changes in microglia upon their activation. Alternatively, the expression of tPA may be detected by employing an anti-tPA antibody composition, such as an antibody linked to a detectable marker. The distribution of the tPA can then be assessed to determine the spatial extent and degree of neuronal degradation. Alternatively, an previous insult to the nervous system, such as a seizure, may be detected, e.g., for pathological analysis.

The invention further includes a method of assessing or diagnosing the susceptibility of a human or animal subject to seizure. In this embodiment, the method involves detecting protease function in the subject. Thus, the method can include measuring the level of tPA expression or activity and comparison of the level to a reference of other test level to ascertain the susceptibility of the subject to seizure. Alternatively, the method can include measuring microglial activation to determine the likelihood that seizure might occur in the patient, or whether such seizure has occurred.

In addition, the invention includes a method of reducing the susceptibility of a human or animal subject to seizure. This embodiment includes inhibiting protease function in nervous tissue of the subject, such as by inhibiting tPA expression or activity, including by inhibiting microglial function. This method is associated with a therapeutic treatment method of the invention which involves inhibiting protease, specifically tPA, function in nervous tissue in a human or animal subject. Thus, the invention includes a method of reducing neuronal degeneration associated with seizure, as well as reducing the extent, frequency and severity of seizure itself.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein.

DETAILED DESCRIPTION OF THE PREFERRED EMBODIMENTS

Figure 1:
FIG. 1 is a photomicrograph showing expression of β-galactosidase in microglial cells.

Neuronal cell death occurs during normal development of the nervous system as well as in various pathological conditions. The molecular mechanisms by which this degeneration occurs have previously been unknown. In addition, the role which tPA plays in neuronal plasticity has previously been unclear. Using excitotoxins to produce neuronal structural changes, we have now unexpectedly found that tPA is required for neuronal degeneration in the hippocampus. Additionally, we have found that, surprisingly, mice which are genetically deficient for tPA are less susceptible to pharmacologically-induced seizure than normal or wild-type mice. Given these new findings, several implications are now evident regarding the neuronal degeneration associated with seizure, and methods by which either or both of these phenomena may be detected and/or inhibited. These results identify a functional role for tPA in neuronal degeneration and remodeling.

It is now established, as described in the Examples provided hereinbelow, that tPA is directly associated with the susceptibility for seizure as well as with the degenerative changes which accompany seizure, and presumably other insults to the nervous system. Accordingly, methods are now available which exploit these relationships for both in vitro and in vivo intervention. Specifically, the invention provides methods of regulating neuronal degeneration and/or seizure, as well as for determining the predisposition of individual human or animal subjects to seizure and neuronal degeneration.

Methods are known for the molecular genetic regulation of structural gene expression. Any of the known methods may be adapted for use in the present invention for the regulation of tPA expression. For example, antisense RNA is a technique which has shown broad applicability both in vitro and in vivo. Specifically, antisense RNA complementary to both coding and noncoding regions of tPA RNA have been shown to selectively block tPA synthesis (Ref. 16). Other methods of controlling tPA expression may also be employed consistent with the present invention. Such methods include, for example, gene transfer techniques in which a gene encoding a less active form of tPA is introduced by virus or other vector into microglial cells (Ref. 17), and regulation of transport and/or release of newly synthesized tPA molecules. Numerous such methods are described, for example, in Meyers, R. A., ed., *Molecular Biology and Biotechnology*, VCH Publishers, Inc., New York (1995) (Ref. 18), the entire disclosure of which is incorporated by reference herein.

More generally, we have now found that microglial activation is directly associated with increase in tPA expression by those cells. It would appear, therefore, that inhibition of microglial activation is a suitable means of accomplishing the stated end of reducing tPA expression. Inhibitors of microglial activation are known. For example, MK-801 inhibits microglial activation and also inhibits tPA expression. MK-801 is a non-competitive antagonist of the NMDA receptor. Presumably, other NMDA receptor inhibitors would effectively inhibit tPA expression.

Alternatively, the method of the invention includes methods of regulating tPA activity once it has been expressed. For example, since tPA is a proteolytic enzyme, like other enzymes it may be inhibited. Both exogenous and endogenous (Ref. 19) inhibitors of tPA are known, which inhibit tPA activity either on a temporary or a permanent basis. One such endogenous inhibitor, plasminogen- activator-inhibitor-1 (PAI-1) is recognized as a potent and specific inhibitor of tPA (Refs. 20–21). Other methods of interfering with tPA activity are also known, including interfering with the interaction of tPA with cellular receptors and intercellular matrix components. Small molecule inhibitors would also be suitable for this purpose.

For inhibiting microglial activation and/or tPA activity or expression, the agents suitable for these effects preferably act substantially selectively, incurring few if any side effects. The mode of administration may be determined by the skilled artisan based on the physical and chemical properties of the active agent. Enteral or parenteral administration is contemplated. Parenteral administration routes include injection, e.g., intravenous injection of the agent in composition with a suitable pharmacologically acceptable diluent together with other active and/or inactive ingredients, excipients, etc. For example, two or more agents active in accordance with the invention may be administered together, thereby achieving additive or even synergistic effects. Typically, inasmuch as the site of action of the agent is desirably in the central nervous system, more preferably the brain, the agent should be capable of reaching the nerve tissue without being substantially impeded by the blood-brain barrier. This permits administration at a site in the body which is convenient and relatively non-invasive. Otherwise, if the agent is not substantially resistant to metabolic degradation or is incapable of traversing the blood brain barrier, direct administration into the affected area or its adjacent tissues may be necessary.

The empirical establishment of the mechanisms which are exploited by the invention are described in detail in the following examples. These examples are illustrative of the utility of the present invention, but do not limit the invention.

EXAMPLE 1
Hippocampal Microglia Produce tPA

Although the expression of tPA in the hippocampus and its induction by pharmacological and electrical stimulation are well-documented (Refs. 7–9), the role for the enzyme in the brain has not been established. Since the four different cell types in the hippocampus-neurons, oligodendrocytes, astrocytes, and microglia-perform distinct functions which might involve proteolytic activity (Ref. 22), defining the site or sites of synthesis of tPA was an essential first-step in determining its function.

The pattern of tPA mRNA expression in the adult mouse hippocampus coincides with the pyramidal (neuronal) cell layer of the CA1 to CA3 regions of the hippocampal formation and the granule cell layer of the dentate gyrus (Ref. 7; and unpublished observations). The intimate association of neurons with their surrounding glia, however, has previously made it difficult to determine unambiguously which cell type expresses tPA.

Transgenic mice (tPA/lacZ) have been generated which carry a mouse tPA promoter fused to the bacterial lacZ gene (Ref. 9). The expression pattern of β-gal in these mice generally reproduced endogenous tPA mRNA expression in the hippocampus both in location and in transcriptional activation after induction of seizure. The resolution of cytoplasmic β-gal staining in the tPA/lacZ transgenic mice made it possible to analyze brain sections for tPA promoter activity in great detail.

A seizure-inducing agent, metrazol (pentylene tetrazol) (50 mg/kg), was administered to tPA/lacZ mice by intraperitoneal injection. After a recovery period of five days, animals were anesthetized and heart perfusion was performed using PBS followed by 4% paraformaldehyde. The brains were removed and left in 30% sucrose in fixative overnight at 4° C. Coronal tissue sections (30 μm) were prepared and stained overnight at 37° C. with X-gal (Ref. 23).

When viewed under high magnification, the hippocampal β-gal staining showed a punctate pattern over the CA1 to CA3 regions and dentate gyrus (DG), but the size of the stained cells was smaller than the pyramidal cell bodies (FIG. 1). Instead, the dimensions of the β-gal producing cells indicated that a subset of microglial cells surrounding the neurons was expressing β-gal and, by inference, tPA mRNA.

EXAMPLE 2

To more clearly exclude the potential contribution of neuronal activity, we eliminated neurons in adult tPA promoter/lacZ mice by unilateral, intracerebral injection of kainic acid (KA). This excitotoxin is a cyclic, glutamate analog that can cause convulsions and neuronal degeneration. To assess neuronal cell death, brain sections were examined by cresyl violet staining of neuronal cell bodies.

Adult male mice, weighing approximately 25 g, were administered atropine (0.6 mg/kg of body weight) by intraperitoneal injection, and then deeply anesthetized with metophane. The anesthetized mice were placed in a stereotaxic apparatus, and administered 1.5 nmol of kainic acid in 0.3 μl of PBS by unilateral injection into the hippocampus (Ref. 13). The coordinates of the injection were: bregma −2.5 mm, medial-lateral 1.7 mm, and dorsoventral 1.6 mm. The kainic acid was delivered over 30 s, with the pipette maintained in place for an additional 2 min to prevent reflux of fluid. After a recovery period of 5 (FIG. 2A) or 16 days (FIGS. 2B or 2C) brain sections were prepared as described in Example 1. The sections were mounted onto slides, dehydrated through increasing ethanol gradients, and then stained. In FIG. 2, panel A was stained with cresyl violet, which stains neuronal cell bodies; panels B and C were stained overnight for β-gal activity and counter-stained with neutral red. For the tPA enzymatic activity assay, wild-type mice administered kainic acid by injection were sacrificed 5 days after the injection. The brains were frozen and processed as described previously (Ref. 7), except that amiloride was not included in the overlay mixture. The photograph was taken under dark field illumination after 2 h incubation at 37 ° C.

Figure 2A:
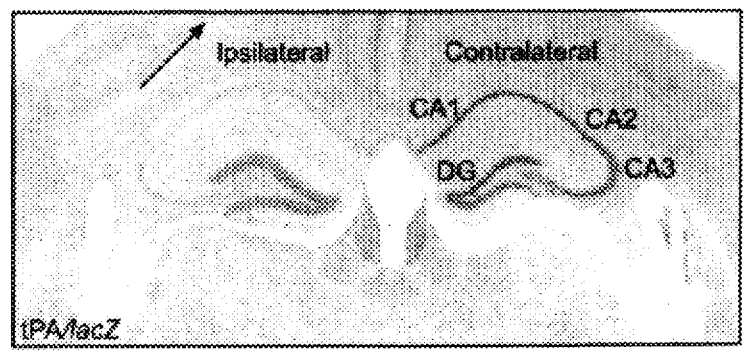
FIGS. 2A–2C are photomicrographs illustrating that tPA/lacZ-expressing cells persist after excitotoxin-induced neuronal loss.
Figure 2B:
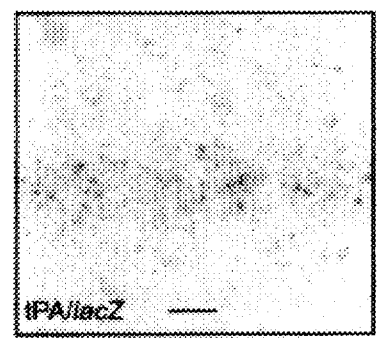
Figure 2C:
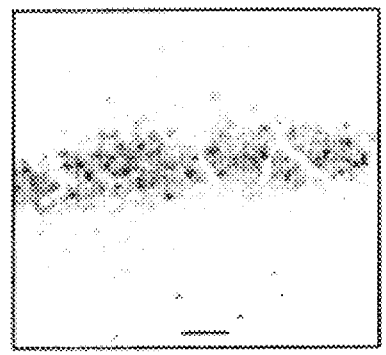
Figure 2D:
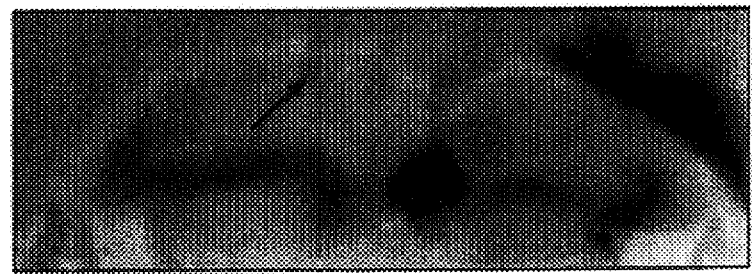
FIG. 2D shows that tPA activity also persists in the absence of neurons.

FIGS. 2A–2C illustrate the persistence of tPA/lacZ-expressing cells following excitotoxin exposure. Low magnification cresyl violet staining of coronal sections through the hippocampus illustrates the lesion generated by 1.5 nmol kainic acid (KA) on the ipsilateral side (side of injection; arrow), whereas contralateral to the lesion no neuronal death was observed. FIG. 2A shows hippocampus from a wild-type tPA/lacZ mouse 5 days after the injection. FIG. 2B shows tissue from a tPA/lacZ mouse: higher magnification of the ipsilateral side, 16 days after injection. FIG. 2C shows tissue from a tPA/lacZ mouse: higher magnification of the contralateral side, 16 days after injection. Scale bar in FIGS. 2B and 2C: 20 μm. Note the persistence of the β-gal staining on the ipsilateral side where the pyramidal cells have been destroyed (FIG. 2B). Given that neuronal cell death is observed within 12 hours following injection, and that the mice were examined at 16 days, it is unlikely that the β-gal staining represents residual, phagocytosed neuronal debris. FIG. 2D shows a tPA histoenzymatic assay on a coronal brain section of a wild-type mouse having had kainic acid injected unilaterally as in FIG. 2A. Note the zone of proteolysis indicating tPA enzymatic activity primarily over the CA2–CA3 hippocampal subfields and DG. The arrow points to the zone of proteolysis surrounding the injection track, where microglia accumulate.

Consistent with previous reports (Ref. 13), complete loss of neuronal cells in the CA1 to CA3 pyramidal cell layers was observed on the ipsilateral (injected) side (FIG. 2A). Granule cells of the dentate gyrus were unaffected by the injection of KA. Similarly, there was no noticeable degeneration on the contralateral (uninjected) side (Ref. 13). When adjacent tissue sections were stained for β-gal, the staining persisted on the ipsilateral side, even though no neuronal cells were present. In addition, the intensity of the staining in the absence of neurons was comparable to that of the unaffected, contralateral side (FIGS. 2B and 2C). This result conclusively shows that tPA is not produced by neurons.

After KA injection, a significant increase of β-gal expression was observed in the dentate gyrus on the ipsilateral side (data not shown). Microglia have been reported to accumulate in the dentate gyrus after injury, even though neuronal death is not observed there (Ref. 14). Since neuronal cell number increase is not observed in the dentate gyrus, this increase in β-gal staining is most likely due to accumulation of microglia.

Taken together, the results shown in Examples 1 and 2 demonstrate that activated microglial cells are the major source of tPA in the hippocampus.

EXAMPLE 3
tPA-Deficient Mice are Resistant to Excitotoxin-Induced Neuronal Degeneration Having determined that tPA is a microglial protease, we investigated whether this enzyme plays a role in the degradation of neurons in the hippocampus. Three different strains of mice were treated by injection of kainic acid: mice homozygous for a disrupted tPA allele ($tPA^{-/-}$) (Ref. 24), and the two inbred, control strains (C57 and 129) that were used to generate the $tPA^{-/-}$ animals.

Figure 3A:
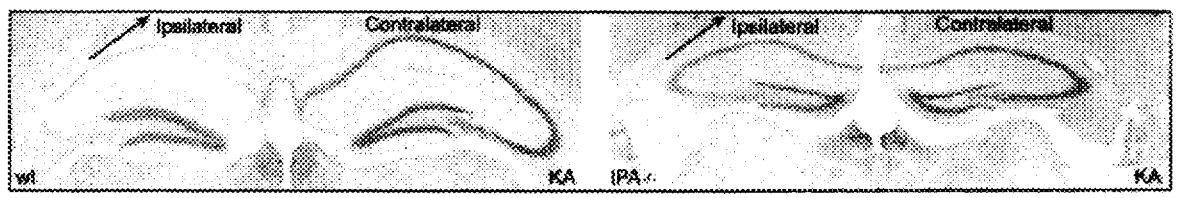
FIG. 3 includes photomicrographs showing that tPA$^{-/-}$ mice are resistant to neuronal degeneration in the hippocampus induced by kainic acid (FIG. 3A), quisqualic acid (FIG. 3B), and quinolinic acid (FIG. 3C).

FIG. 3A includes two photomicrographs showing low magnification cresyl violet staining of coronal sections through the hippocampus. The injection of kainic acid was performed as described in Example 2. The brains of the treated mice were analyzed 5 days after injection. The left hand panel in FIG. 3A shows tissue from a wild-type 129 mouse; the right-hand panel shows tissue from a $tPA^{-/-}$ mouse. The substantial destruction of the neurons in all of the CA fields in the control mouse (FIG. 3A, left) contrasts sharply against the extent of neuron survival in the $tPA^{-/-}$ mouse (FIG. 3A, right). The experiment was repeated with 8 C57 mice, 4 129 mice, and 12 $tPA^{-/-}$ mice.

Figure 3B:
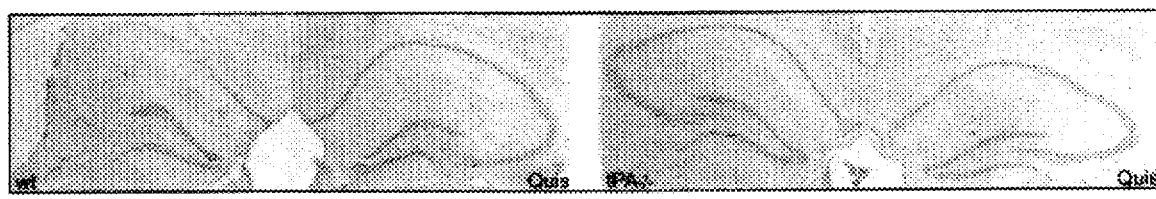

In control animals, essentially complete neuronal loss was observed in the CA1 to CA3 regions, similar to that of the tPA/lacZ mice (strain 129, FIG. 3A, left; strain C57, data not shown). By contrast, neuronal degeneration in the hippocampus of $tPA^{-/-}$ mice was minimal (FIG. 3B, right). (These results are confirmed quantitatively in FIG. 4A.) Although the degeneration observed in the $tPA^{-/-}$ mice was dramatically reduced, some cell loss was evident close to the injection site, suggesting that the lack of tPA increases the threshold necessary to effect degeneration.

Figure 3C:
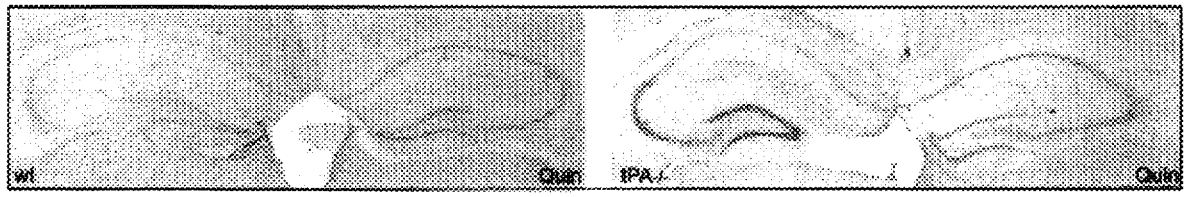

Kainic acid is an agonist of one subtype of the glutamate receptor system, but there are other classes of glutamate gated ion channels: (2-aminomethyl)phenylacetic acid (AMPA) and N-methyl-D-aspartate (NMDA). To determine if the lack of neuronal loss observed was specific for the KA subtype of glutamate receptors, we injected intracerebrally agonists whose action is mediated through the AMPA or NMDA receptors. Quisqualate (20 nmol) and quinolinate (120 nmol) were injected into $tPA^{-/-}$ mice as described in Example 2. The brains of the treated mice were examined 5 days after injection. FIGS. 3B and 3C include photomicrographs comparable to those described for FIG. 3A, with tissue from the wild-type mouse in the left-hand panels and tissue from the $tPA^{-/-}$ mice in the right-hand panels. Significant resistance to cell death was observed in $tPA^{-/-}$ mice after injection of quisqualate (AMPA receptors) (FIG. 3B) or quinolinate (NMDA receptors) (FIG. 3B). These experiments were repeated with 2 C57 and 2 $tPA^{-/-}$ mice for quisqualate, and 2 C57 and 2 $tPA^{-/-}$ mice for quinolinate.

EXAMPLE 4

The data illustrated qualitatively in FIGS. 3A-3C were quantified as follows: Two wild-type (wt) and two $tPA^{-/-}$ mice for each excitotoxin were treated and the tissue processed as described above. Serial sections (30 μm) were prepared and stained with cresyl violet. Five or six matched sections from the dorsal hippocampus of wild-type and $tPA^{-/-}$ mice were drawn with a camera lucida and subjected to quantitative analysis; the linear distances of spared (intact) (black), partly lost (white), and totally lost (grey) pyramidal cell layer were determined on each section. Distances were digitized from the camera lucida drawings of the hippocampus. The measurements for each category over each hippocampal region were averaged across subjects in a group and plotted.

Figure 4B:
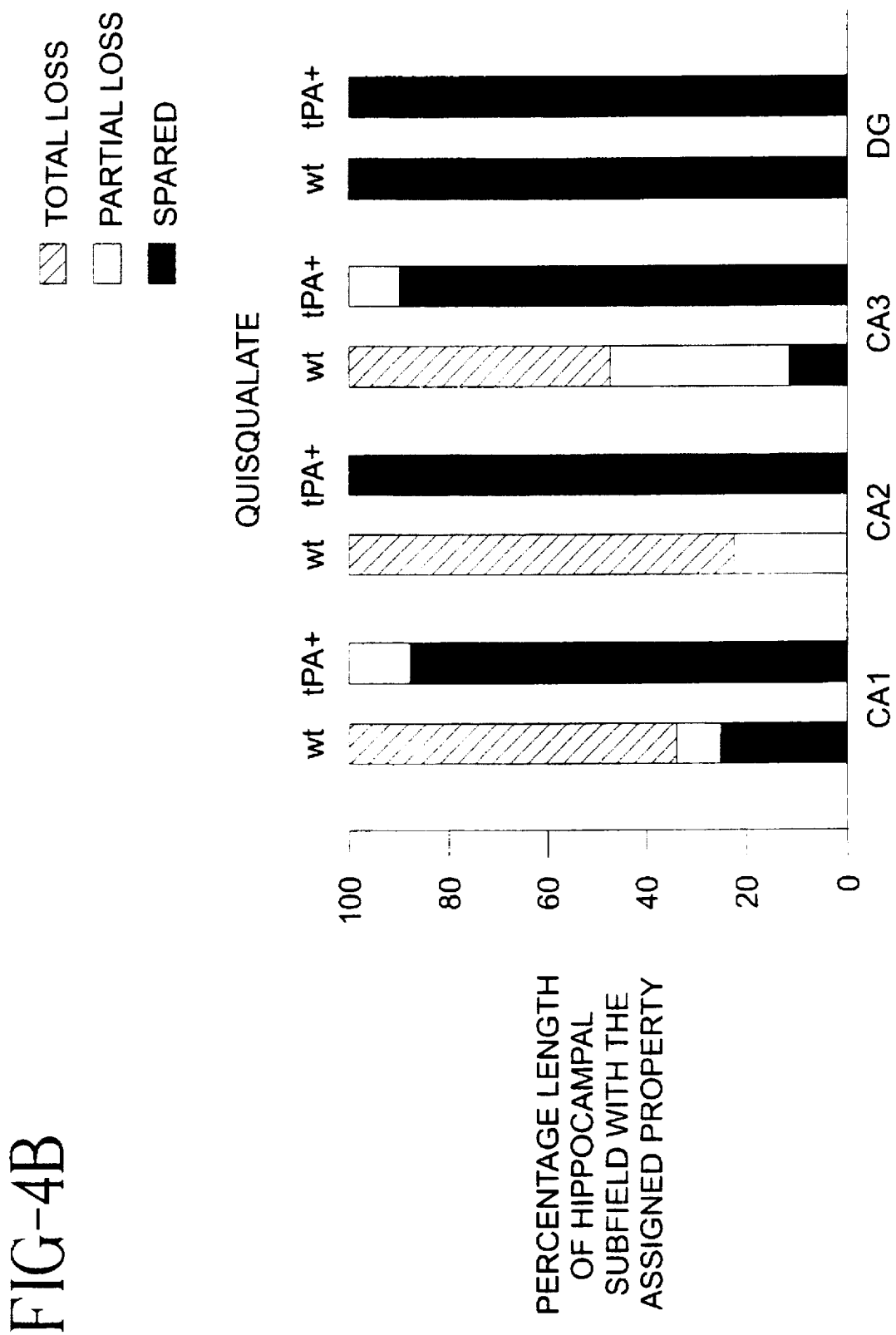
FIG. 4 includes graphs shows the quantitation of the resistance of tPA$^{-/-}$ mice to neuronal degeneration induced by kainic acid (FIG. 4A), quisqualic acid (FIG. 4B), and quinolinic acid (FIG. 4C).
Figure 4C:
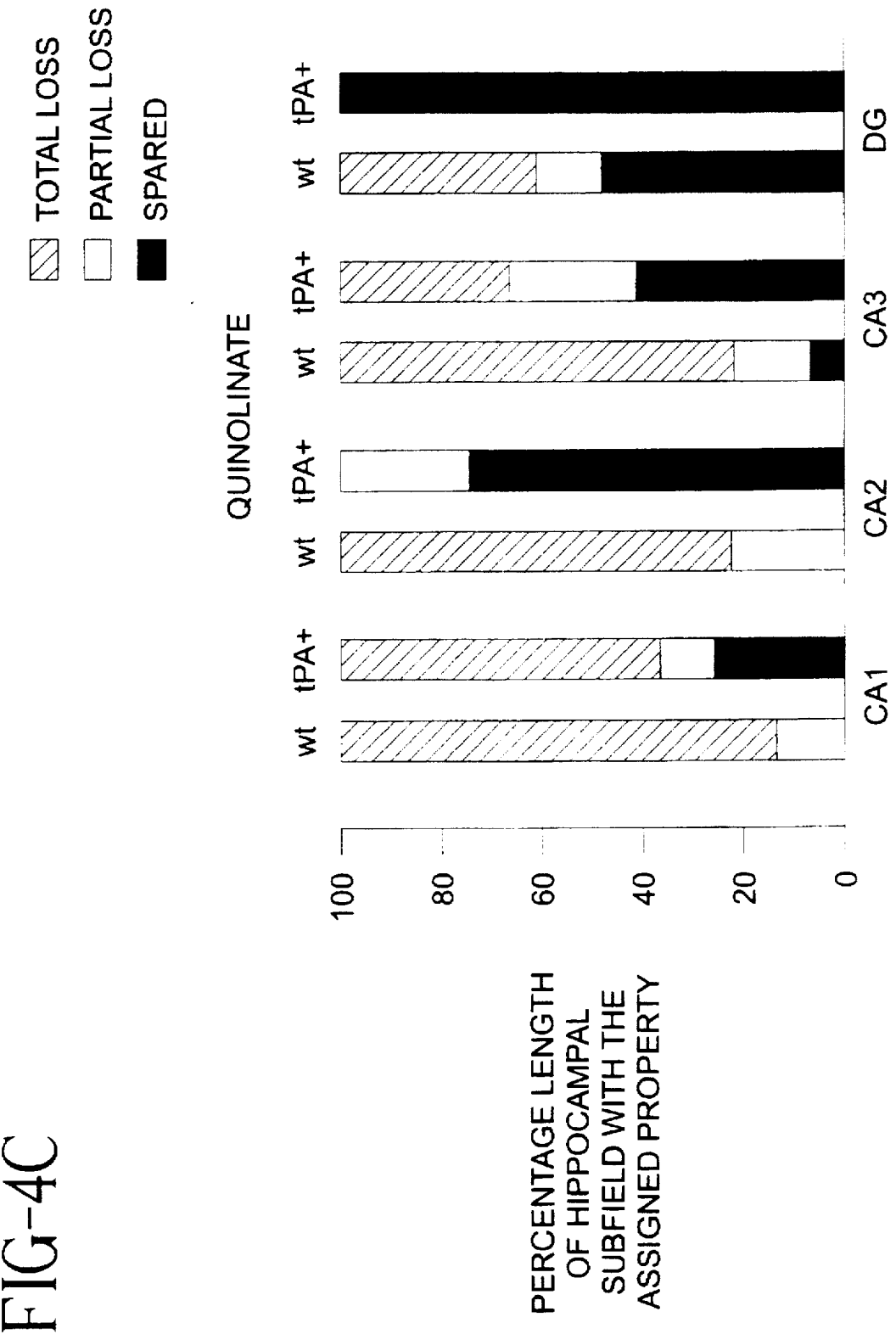

FIGS. 4A-4C show the results of this analysis: kainate (FIG. 4A); quisqualate (FIG. 4B); and quinolinate (FIG. 4C). The linear distance of spared, partly degenerated, or completely lost neurons was measured in matched coronal sections at different rostrocaudal levels of the dorsal hippocampus. In each case the absence of tPA conferred dramatic resistance. For example, in KA-injected animals, C57 control mice demonstrated 66% loss of CA1, 38% loss of CA2, and 77% loss of CA3 neurons. Matched sections of $tPA^{-/-}$ mice showed no neuronal loss in CA1 or CA2, and only 15% loss in CA3 neurons. Similar levels of resistance were observed with quisqualate and quinolinate.

The results described in Examples 3 and 4 implicate tPA as a key factor in the neuronal disappearance induced by excitotoxin. The decrease in neuronal cell death in $tPA^{-/-}$ mice is observed in relation to a wide range of excitotoxins. This implies that various glutamate receptor antagonists may be employed according to the method of the invention to regulate neuronal degeneration.

EXAMPLE 5
Attenuated Activation of Microglia in $tPA^{-/-}$ Mice

The lack of neuronal degeneration in KA-injected $tPA^{-/-}$ mice could be due to a failure of microglial cell activation, which might result in neuronal persistence. To address this question, brain sections after KA injection were immunostained for the microglial-specific antigen F4/80, which is produced only after activation (Ref. 25).

Kainic acid injection was performed as described in Example 2. The brain sections of the treated mice were immunostained with the activated microglia-specific polyclonal antibody F4/80 as described in Example 1.

Figure 5A:
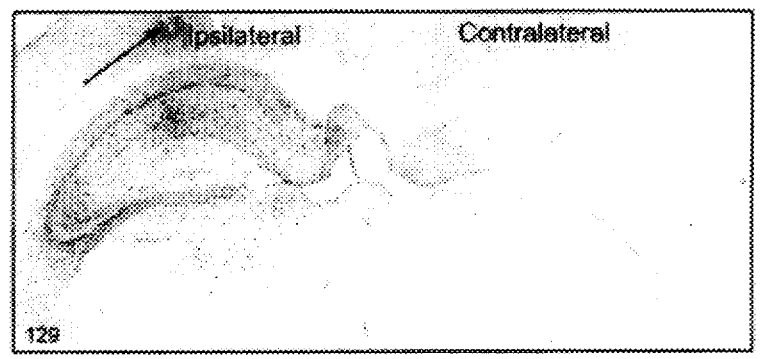
FIGS. 5A–5D are photomicrographs showing that microglia in tPA$^{-/-}$ mice become activated after injection of kainic acid.
Figure 5B:
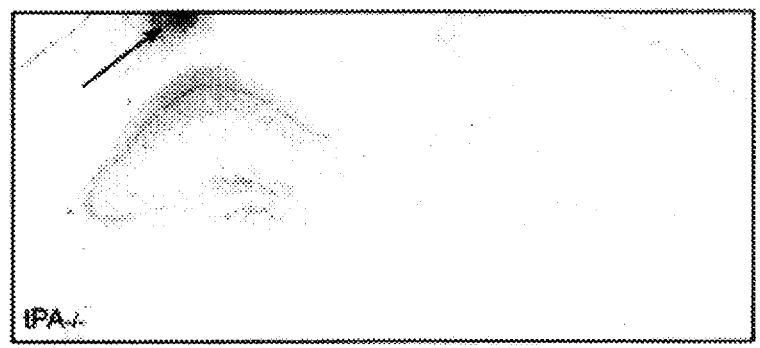
Figure 5C:
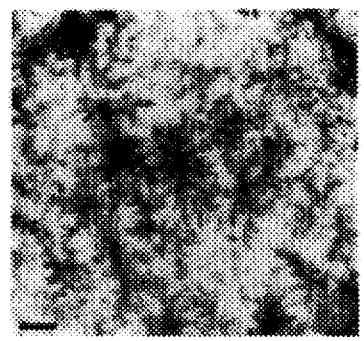
Figure 5D:
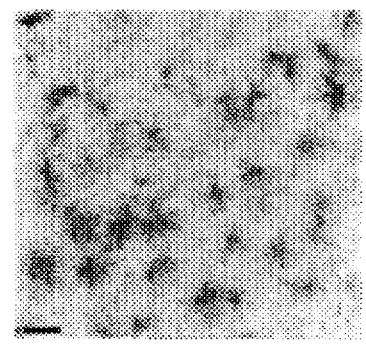

FIGS. 5A-5D are low magnification photomicrographs of F4/80 immunostaining of coronal sections through the hippocampus 5 days post-injection. FIG. 5A shows tissue of a 129 mouse; FIG. 5B shows tissue of a $tPA^{-/-}$ mouse. Maximal activation is observed on the ipsilateral side and around the injection site (arrow). Microglia on the contralateral side are activated as well, but to a lower level. FIG. 5C is a high magnification micrograph of representative activated microglia in the CA1 field of stratum radiatum on the ipsilateral side of a 129 mouse. FIG. 5D is a high magnification micrograph of activated microglia of $tPA^{-/-}$ mouse. Scale bar: 20 μm.

Qualitatively, microglia from all three mouse strains behaved similarly: the cells were activated around the injection site and along the pyramidal cell layers of CA1 to CA3, whereas no activation was observed on the uninjected side (FIGS. 5A and 5B) (Ref. 13). Activated microglia were also observed in the deep portion of the dentate granule cell layer of the basket pyramidal cells. These cells are not susceptible to excitotoxicity and are thus spared from degeneration (Ref. 14).

Despite qualitative similarity, however, quantitatively, the extent of immunostaining observed in $tPA^{-/-}$ mice was decreased compared to that in C57 or 129 mice. The intensity of F4/80 staining suggests an approximately 2-fold lower degree of microglial activation in $tPA^{-/-}$ mice. This difference in intensity is less dramatic than the difference in neuronal persistence in the hippocampal CA pyramidal fields.

Microglial activation can also be assessed by morphology. In the hippocampus of wild-type mice, resident microglia have a characteristic radially-branched shape (Ref. 25). After injection of KA, microglial cell number increases and their processes become increasingly arborized (Ref. 13). The activation of microglia in $tPA^{-/-}$ mice was evaluated using these morphological criteria. An attenuation in morphological changes was observed when $tPA^{-/-}$ mice were compared to C57 (data not shown) and 129 mice (FIGS. 5C and 5D). All of these indicate that tPA is involved in the activation pathway of microglial cells.

EXAMPLE 6
$tPA^{-/-}$ Mice are Resistant to Chemically-Induced Seizure

After intracerebral injection of KA, control mice underwent epileptic seizures in the immediate post-operative period, consistent with the reported effect of injection of the excitotoxin (Ref. 26). In contrast, at this dose of KA, the $tPA^{-/-}$ mice did not exhibit overt seizures.

We investigated this observation further by determining the responses of these mice to increasing concentrations of seizure-inducing agents. Metrazol, a convulsant drug that acts through a GABA receptor and increases the transcription of tPA in the hippocampus (Refs. 8, 9), was injected intraperitoneally into $tPA^{-/-}$ and control mice at the indicated concentration. Kainate was injected as described above into another group of $tPA^{-/-}$ and control mice. Convulsive behavior as observed within five minutes from the time of injection in the C57 or 129 mice. The onset of seizure for $tPA^{-/-}$ mice usually occurred approximately 15-20 minutes after metrazol delivery.

Seizures were classified using the following five categories (Ref. 27): 1, arrest of motion; 2, myoclonic jerks of the head and neck, with brief twitching movements; 3, unilateral clonic activity; 4, bilateral forelimb tonic and clonic activity; 5, generalized tonic/clonic activity with loss of postural tone. To control against potential bias in interpretation of mouse behavior, the labels indicating the mouse strains were removed from the cages and replaced by numbers. The behavior of the mice was monitored by non-biased, "blind" judges.

Figure 6A:
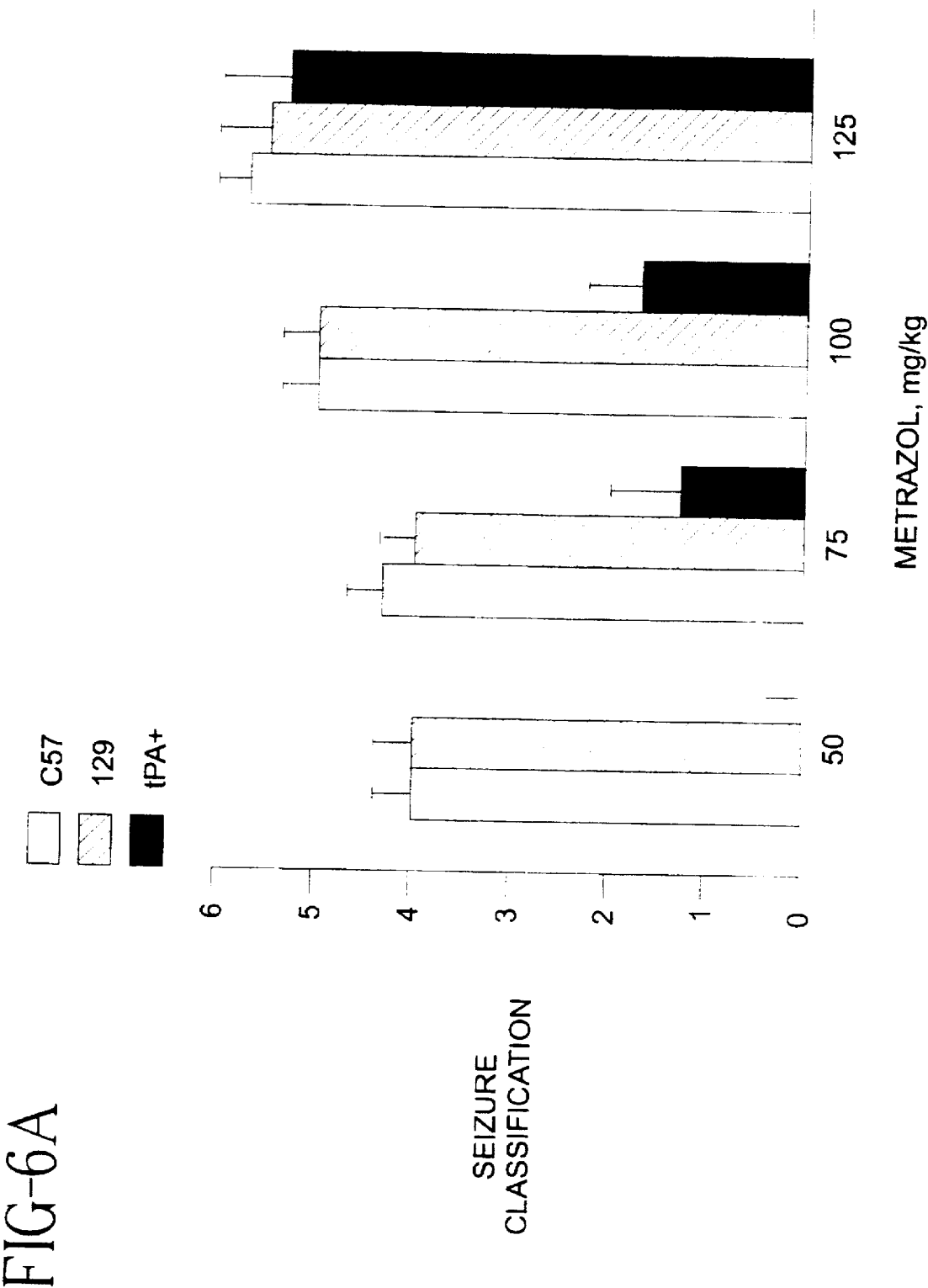
FIGS. 6A–6B are graphs illustrating the types of convulsive behavior of mice treated with seizure-inducing quantities of metrazol (FIG. 6A) or kainate (FIG. 6B).
Figure 6B:
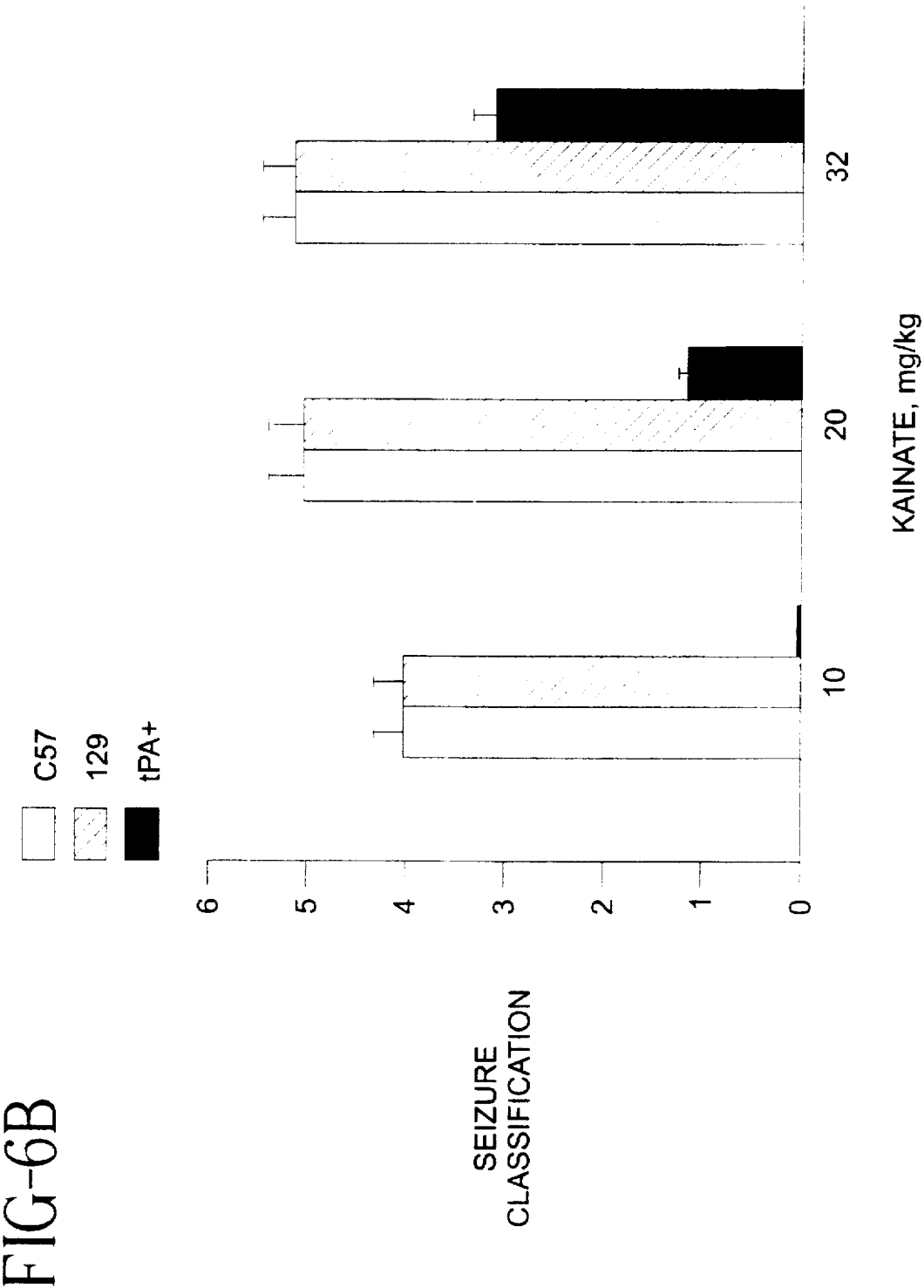

The $tPA^{-/-}$ mice had a higher threshold with respect to both metrazol-seizure induction (FIG. 6A) and kainate-seizure induction (FIG. 6B) as compared with the control strains. This resistance to seizure induction was evident with respect to the dose of agent, as well as with respect to the time delay between drug delivery and the onset of seizure (data not shown). Since one consequence of seizure is neuronal degeneration (Ref. 28), it is consistent that the $tPA^{-/-}$ mice are resistant to both processes.

Conclusions

Our data show that $tPA^{-/-}$ mice are resistant to neuronal degeneration and seizure after excitotoxin injection. The brains of the $tPA^{-/-}$ mice were examined in detail, and no obvious morphological abnormalities were detected (Ref. 24, and unpublished observations). Therefore, it is probable that the observed effects are due to lack of expression of tPA in the adult hippocampus. However, embryonic development in the absence of tPA might cause subtle alterations in the cytoarchitecture or circuitry of the brain, which could result in the observed phenotypes. With this reservation in mind, it is interesting to consider the effect of tPA on neurodegeneration and seizure from several points of view: 1, the role of microglia cells and their activation; 2, the molecular mechanism by which tPA influences degeneration; 3, the relationship of tPA to other mutations implicated in altered seizure susceptibility; 4, the possibility that tPA plays a role in normal hippocampal plasticity; and 5, possible insights into neurodegenerative diseases and their treatment.

Previous evidence indicates that microglial protease activity is in certain circumstances related to neuronal survival. Specifically, transection of the optic nerve leads to degeneration of ganglion cells, and injection of protease inhibitors into the vitreous body retards this degeneration (Ref. 15). The results described above now strongly suggest that microglial protease activity is attributable to tPA, and that tPA is synthesized not simply in response to dying neurons, but is directly involved in the destruction of those neurons.

The fact that microglial activation is reduced in $tPA^{-/-}$ mice could partially explain the lack of neuronal degeneration. This decrease could be due to a diminished response of the hippocampal cells to KA. In general, the activation mechanism of microglia cells is not well defined. It is known that microglial activation is blocked by the NMDA receptor antagonist, MK-801 (Ref. 14), and that the transcriptional induction of tPA is also inhibited by MK-801 (Ref. 8). These results, along with the attenuated microglial activation in the $tPA^{-/-}$ mice, indicate that activation and expression of tPA may be related.

The molecular mechanism by which tPA influences neuronal degeneration is not known. The only defined substrate for tPA is the zymogen plasminogen. Plasminogen might be increased in the brain since injury results in a compromised blood-brain barrier (Ref. 29); alternatively, local synthesis of plasminogen is possible, since its mRNA is detected in the brain (Ref. 7) and microglia in culture secrete plasminogen (Ref. 30). If plasminogen is present, a classical cascade could be generated that would greatly amplify the proteolytic potential and promote tissue remodeling.

These considerations raise the issue of what the ultimate target for the proteolytic activity might be, and how this process might regulate neuronal survival. Activated microglia in culture secrete neurotoxic molecules that may be responsible for the death of neurons after CNS injury (Ref. 31). It is possible that tPA and/or plasmin mediate the synthesis or processing of molecules with neurotoxic properties. If so, tPA would have a dual role in affecting both microglial activation and the generation of neurotoxins, and its absence would result in dramatic persistence of neurons.

Our observation of the resistance of $tPA^{-/-}$ mice to seizure identifies this protease as a participant in the convulsive pathway that alters seizure susceptibility. There are other genetically-defined mutations that appear to reside in a single gene and which predispose mice to convulsions (Refs. 32, 33). Since seizure susceptibility is genetically complex (Refs. 34, 35), it will be interesting to determine the extent to which the tPA gene interacts with other loci associated with inherited convulsive disorders.

It has been hypothesized that the morphological changes that occur after kindling and seizures are an exaggerated form of the structural changes that take place during long-term potentiation and learning/memory (Ref. 2). In this context, although tPA$^{-/-}$ mice do not exhibit any severely abnormal phenotype (Ref. 24), evidence has been presented that they display deficits in spatial learning, as tested by the Morris swimming navigation task (Ref. 36). Therefore, it appears consistent that the deficiency for tPA could lead to both learning impairment and seizure resistance.

Urokinase-type plasminogen activator (uPA), another form of plasminogen activator, is not normally found in the mouse hippocampus (Refs. 6, 7). However, ectopic expression of this enzyme in the brain of transgenic mice results in compromised learning abilities (Ref. 37). This finding, along with the acquisition/learning deficits of the tPA$^{-/-}$ mice, suggests that a delicate proteolytic balance may be necessary to ensure both maintenance and appropriate modulation of neuronal connections, which are required for normal learning memory capacities.

There is extensive neuronal degeneration in the hippocampus in various pathological situations, e.g., in Alzheimer's disease, in ischemia of the brain due to reduced blood flow, and in epilepsy (Ref. 5). While apoptosis-related mechanisms can explain some of these pathologies, it has not been established yet if they are involved in KA-induced nerve cell death (Refs. 26, 38). Our work has now identified tPA as a necessary link in experimentally-induced neuronal degeneration and seizure, and reaffirms that over-expression of tPA activity could contribute to neuronal destruction in some of these diseases. In this respect, Alzheimer amyloid β-peptide analogs have recently been found to stimulate tPA activity in vitro (Ref. 39), further suggesting that elevated protease activity may be related to this pathology. Therefore, over-expression of tPA in the hippocampus might lead to an in vivo mouse model of neuronal degeneration and/or susceptibility to seizure. Such a model would be useful for testing whether inhibitors of tPA might be used to prevent destruction and seizure, induced either by excitotoxins or inherited genetic mutations. Such inhibitors constitute a new class of compounds with therapeutic and diagnostic activity.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

BIBLIOGRAPHY

1. Desmond, N. and Levy, W., *Synapse* 5:139–143 (1990).
2. Baudry, M., in *Adv. Neurol.* (eds. Delgrado-Escueta, A., Treiman, D., Ward, A. J., Woodbury, D. and Porter, R.) 401–410, Raven Press, New York (1986).
3. Selkoe, D., *Trends Neurosci.* 16:403–409 (1993).
4. Saitoh, T., et al., *Annals NY Acad. Sci.* 674:180–192 (1992).
5. Siman, R., *Annals NY Acad. Sci.* 674:193–202 (1992).
6. Rickles, R. and Strickland, S., *FEBS Letters* 229:100–106 (1988).
7. Sappino, A., et al., *J. Clin. Inves.* 92:679–685 (1993).
8. Qian, Z., Gilbert, M., Colicos, M., Kandel, E. and Kuhl, D., *Nature* 361:453–457 (1993).
9. Carroll, P., Tsirka, S., Richards, W., Frohman, M. and Strickland, S., *Development* 120:3173–3183 (1994).
10. Krystosek, A. and Seeds, N., *Science* 213:1532–1534 (1981).
11. Salles, F., Schechter, N. and Strickland, S. *EMBO J* 9:2471–2477 (1990).
12. Krystosek, A. and Seeds, N., *Proc. Natl. Acad. Sci. (U.S.A)* 78:7810–7814 (1981).
22. Kandel, E., Schwartz, J. and Jessel, T. Principles of Neural Science (Elsevier Science Publishing Co., Inc., New York, N.Y., 1991).
13. Andersson, P., Perry, V. and Gordon, S. *Neurosci.* 42:201–214 (1991).
14. Streit, W., *J. Clin. Neuroanat.* 6:261–266 (1993).
15. Thanos, S., *Eur. J. Neurosci.* 3:1189–1207 (1991).
16. Strickland, S., Huarte, J., Belin, D., Vassalli, A., Rickles, R. J., and Vassalli, J. D., *Science* 241:680–684 (1988).
17. Lee, S. W., Kahn, M. L., and Dichek, D. A., *Trends Cardiovasc. Med.* 3:61–66 (1993).
18. Meyers, R. A., ed., *Molecular Biology and Biotechnology*, VCH Publishers, Inc., New York (1995).
19. Gerard R. D., Chien, K. R., and Meidell, R. S., *Mol. Biol. Med.* 3:449–457 (1986).
20. Collen, D., Chapter 1 in *Tissue Plasminogen Activator* in Thrombolytic Therapy, (eds. Sobel, B. E., Collen, D., and Grossbard, E. B.), Marcel Dekker, Inc., New York (1987).
21. Bindal, A. K., Hammoud, M., Shi, W. M., Wu, S. Z., Sawaya, R., and Rao, J. S., *J. Neurooncol.* 22(2):101–110 (1994).
23. Smeyne, R., et al., *Neuron* 8:13–23 (1992).
24. Carmeliet, P., et al., *Nature* 368:419–424 (1994).
25. Lawson, L., Perry, V., Dri, P. and Gordon, S. *Neurosci.* 39:151–170 (1990).
26. Pollard, H., et al., *Neurosci.* 63:7–18 (1994).
27. Golarai, G., Cavazos, J. and Sutula, T., *Brain Res.* 593:257–264 (1992).
28. Ben-Ari, Y. and Represa, A., *Trends Neurosci.* 13:312–318 (1990).
29. Pont, F., Collet, A. and Lallement, G., *Neurosci. Lett.* 184:52–54 (1995).
30. Nakajima, K., Tsuzaki, N., Nagata, K. Takemoto, N. and Kohsaka, S., *FEBS Letters* 308:179–182 (1992).
31. Giulian, D., Vaca, K. and Corpuz, M., *J. Neurosci.* 13:21–36 (1992).
32. Kostopoulos, G., *J. Neural Transm.* 35:21–36 (1992).
33. Noebels, J., Qiao, X., Bronson, R., Spences, C. and Davisson, M., *Epilepsy Res.* 7:129–135 (1990).
34. Frankel, W., Taylor, B., Noebels, J. and Lutz, C., *Genetics* 138:481–489 (1994).
35. Martin, B., Marchaland, C., Chapouthier, G. and Motta, R., *Behav. Genet.* 24:285–297 (1994).
36. Lipp, H., et al., *Soc. Neurosci. Abstr.* 19:799 (1993).
37. Meiri, N., Masos, T., Rosenblum, K., Miskin, R. and Dudai, Y., *Proc. Natl. Acad. Sci. (USA)* 91:3196–3200 (1994).
38. Ignatowicz, E., Vezzani, A., Rizzi, M. and D'Incalci, M., *Neuroreport* 2:651–654 (1991).
39. Kingston, I., Castro, M. and Anderson, S., *Nature Medicine* 1:138–142 (1995).

What is claimed is:

1. A method of reducing neuronal degeneration, comprising:
   inhibiting the activity of tPA in nervous tissue of a human or animal subject having an injury to nervous tissue.
2. The method of claim 1, wherein said inhibiting comprises administering to said subject an effective amount of a tPA inhibitor.
3. The method of claim 2, wherein said tPA inhibitor is capable of traversing the blood brain barrier and said administering step comprises introducing said tPA inhibitor at a site remote from said nervous tissue.

4. The method of claim 2, wherein said administering step comprises injecting said tPA inhibitor into said nervous tissue.

5. The method of claim 1, wherein said inhibiting comprises inhibiting microglial activation by administering to said subject an effective amount of a microglia activation inhibitor.

6. The method of claim 5, wherein said microglia activation inhibitor is a glutamate receptor antagonist.

7. The method of claim 6, wherein said glutamate receptor antagonist is MK-801.

8. The method of claim 1, wherein said nervous tissue comprises central nervous system tissue.

9. The method of claim 8, wherein said tissue comprises brain tissue.

10. The method of claim 9, wherein said tissue comprises hippocampal tissue.

11. The method of claim 1, wherein the injury to the nervous tissue is characteristic of seizure, ischemia, epilepsy, or Alzheimer's disease.

12. A method of reducing the susceptibility of a human or animal subject to seizure, comprising:

inhibiting protease activity in nervous tissue of said subject.

13. A method of reducing neuronal degeneration associated with seizure in a human or animal subject, comprising inhibiting, in a human or animal subject which is subject to seizure, at least one of:

a) protease activity in nervous tissue of said subject; and b) microglial activation in nervous tissue of said subject;

whereby neuronal degeneration associated with seizure is reduced in said subject.

14. A method of reducing seizure in a human or animal subject, comprising inhibiting one of:

a) protease activity in nervous tissue of said subject; and b) microglial activation in nervous tissue of said subject.

15. The method of claim 12, wherein said inhibiting of protease activity comprises administering to said subject an effective amount of a tPA-inhibitory compound.

16. The method of claim 12, wherein said inhibiting of protease activity comprises inhibiting microglial activation in said nervous tissue by administering to said subject an effective amount of a compound that inhibits activation of microglia.

* * * * *